US011103547B2

(12) United States Patent
Hayouka

(10) Patent No.: US 11,103,547 B2
(45) Date of Patent: Aug. 31, 2021

(54) METHODS FOR DISRUPTING BIOFILMS

(71) Applicant: Yissum Research Development Company of the Hebrew University of Jerusalem Ltd., Jerusalem (IL)

(72) Inventor: Zvi Hayouka, Mazkeret Batya (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 0 days.

(21) Appl. No.: 16/074,985

(22) PCT Filed: Feb. 2, 2017

(86) PCT No.: PCT/IL2017/050122
§ 371 (c)(1),
(2) Date: Aug. 2, 2018

(87) PCT Pub. No.: WO2017/134661
PCT Pub. Date: Aug. 10, 2017

(65) Prior Publication Data
US 2019/0038701 A1 Feb. 7, 2019

Related U.S. Application Data

(60) Provisional application No. 62/291,117, filed on Feb. 4, 2016.

(51) Int. Cl.
| | |
|---|---|
| *A61K 31/785* | (2006.01) |
| *A61L 2/232* | (2006.01) |
| *B65B 55/00* | (2006.01) |
| *C08G 69/10* | (2006.01) |
| *A61K 38/03* | (2006.01) |
| *A61K 38/16* | (2006.01) |
| *A61L 2/00* | (2006.01) |
| *A61P 31/04* | (2006.01) |
| *A61L 2/18* | (2006.01) |

(52) U.S. Cl.
CPC ............ *A61K 38/03* (2013.01); *A61K 31/785* (2013.01); *A61K 38/16* (2013.01); *A61L 2/0088* (2013.01); *A61L 2/18* (2013.01); *A61L 2/232* (2013.01); *A61P 31/04* (2018.01); *B65B 55/00* (2013.01); *C08G 69/10* (2013.01)

(58) Field of Classification Search
CPC ... A23L 3/34635; A23L 3/3526; A61K 31/74; A61K 31/785; A61K 38/03; A61K 38/16; A61L 2/0088; A61L 2/16; A61L 2/18; A61L 2/232; A61P 31/04; B65B 55/00; B65B 55/02; B65B 55/10; B65B 55/24; C07K 4/00; C07K 14/00; C08G 69/00; C08G 69/10
See application file for complete search history.

(56) References Cited

U.S. PATENT DOCUMENTS

| | | | |
|---|---|---|---|
| 6,172,038 B1 | 1/2001 | Shai et al. | |
| 8,609,608 B2 * | 12/2013 | He | A61K 8/64 514/2.6 |
| 9,499,594 B2 | 11/2016 | Schuch et al. | |
| 2004/0018242 A1 * | 1/2004 | Cunningham | A61K 9/145 424/489 |
| 2009/0053278 A1 * | 2/2009 | Fatora | A61K 38/08 424/423 |
| 2014/0309162 A1 * | 10/2014 | Park | C07K 5/1019 514/2.4 |
| 2015/0344916 A1 * | 12/2015 | Lynch | C12P 11/00 435/135 |
| 2015/0361140 A1 * | 12/2015 | Kim | C07K 7/06 514/17.7 |
| 2015/0374675 A1 * | 12/2015 | Tardif | C07D 241/18 514/330 |

FOREIGN PATENT DOCUMENTS

| | | |
|---|---|---|
| WO | 2010/112848 A2 | 10/2010 |
| WO | 2011/121289 A2 | 10/2011 |
| WO | 2014/035345 A1 | 3/2014 |
| WO | WO-2016161997 A1 * | 10/2016 ............... C07K 7/08 |

OTHER PUBLICATIONS

Stern et al. Random peptide mixtures inhibit and eradicate methicillin-resistant *Staphylococcus aureus* biofilms. Chemical Communications. Apr. 27, 2016, vol. 52, pp. 7102-7105, plus Supporting Information. (Year: 2016).*
Chen et al. Antibacterial activity of short hydrophobic and basic-rich peptides. American Journal of Veterinary Research. Sep. 2003, vol. 64, No. 9, pp. 1088-1092. (Year: 2003).*
Lim et al. Immobilization Studies of an Engineered Arginine-Tryptophan-Rich Peptide on a Silicone Surface with Antimicrobial and Antibiofilm Activity. ACS Applied Materials and Interfaces. Jun. 12, 2013, vol. 5, pp. 6412-6422. (Year: 2013).*
Bahar et al., (2013) Antimicrobial Peptides. Pharmaceuticals (Basel) 6(12): 1543-1575.
Dane et al., (2014) Synthesis of bioinspired carbohydrate amphiphiles that promote and inhibit biofilms. Chem Sci 5: 551-557.
De la Fuente-Núñez et al., (2012) Inhibition of bacterial biofilm formation and swarming motility by a small synthetic cationic peptide. Antimicrob Agents Chemother 56(5): 2696-2704.
De la Fuente-Núñez et al., (2014) Broad-spectrum anti-biofilm peptide that targets a cellular stress response. PLoS Pathog 10(5): e1004152; 12 pages.

(Continued)

Primary Examiner — Jeffrey E. Russel
(74) Attorney, Agent, or Firm — Allan A. Fanucci

(57) ABSTRACT

Provided are methods for disrupting biofilms and/or preventing the formation of biofilms. Further provided are random-sequence peptide mixtures for use in disrupting bacterial biofilms. The random-sequence peptides include hydrophobic and/or cationic amino acids, and the ratio of the total hydrophobic and cationic amino acids in the mixture is predefined.

17 Claims, 9 Drawing Sheets

(56) References Cited

OTHER PUBLICATIONS

Donlan (2002) Biofilms: microbial life on surfaces. Emerg Infect Dis 8(9): 881-890.
Hayouka et al., (2013) Interplay among Subunit Identity, Subunit Proportion, Chain Length, and Stereochemistry in the Activity Profile of Sequence-Random Peptide Mixtures. J Am Chem Soc 135(32): 11748-11751.
Jorge et al., (2012) New trends in peptide-based anti-biofilm strategies: a review of recent achievements and bioinformatic approaches. Biofouling 28(10): 1033-1061.
Lewis (2001) Riddle of biofilm resistance. Antimicrob Agents Chemother 45(4): 999-1007.
Mishra et al., (2015) Small lipopeptides possess anti-biofilm capability comparable to daptomycin and vancomycin. RSC advances, 5(73), 59758-59769.
O'Toole et al., (1998) Flagellar and twitching motility are necessary for Pseudomonas aeruginosa biofilm development. Mol Microbiol 30(2): 295-304.
Stern et al., (2016) Random peptide mixtures inhibit and eradicate methicillin-resistant *Staphylococcus aureus* biofilms. Chem Commun 52: 7102-7105 and supporting information.
Weisblum et al., (1969) Erythromycin-inducible resistance in *Staphylococcus aureus*: survey of antibiotic classes involved. J Bacteriol 98(2): 447-452.

\* cited by examiner

METHODS FOR DISRUPTING BIOFILMS

FIELD OF THE INVENTION

The present invention relates to methods for disrupting biofilms. In particular, the present invention relates to random-sequence synthetic peptide mixtures for use in disrupting biofilms and/or preventing the formation of biofilms.

BACKGROUND OF THE INVENTION

Biofilm is an assemblage of surface-associated microbial cells that are enclosed in an extracellular polymeric substance matrix. Biofilms being formed when bacteria adhere to surfaces in aqueous environments and begin to excrete a slimy, glue-like substance that can anchor them to all kinds of materials, such as metals, plastics, soil particles, medical implant materials and, most significantly, human or animal tissues. Biofilms are composed primarily of microbial cells and extracellular polymeric substance (EPS) matrix. EPS may account for 50% to 90% of the total organic carbon of biofilms and can be considered the primary matrix material of the biofilm. EPS may vary in chemical and physical properties, but it is primarily composed of polysaccharides. Additional biofilm substances are excreted proteins and nucleic acids. The extracellular matrix protects the microorganisms embedded within the biofilm and facilitates the communication between microorganisms through biochemical signals.

Clinical and public health microbiologists' recognition that microbial biofilms are ubiquitous in nature has resulted in the study of a number of infectious diseases from a biofilm perspective. For example, cystic fibrosis, native valve endocarditis, otitis media, periodontitis, and chronic prostatitis, are all appear to be caused by biofilm-associated microorganisms. In addition, a spectrum of indwelling medical devices or other devices used in the health-care environment have been shown to harbor biofilms, resulting in measurable rates of device-associated infections.

*Staphylococcus aureus* (*S. aureus*) is one of the most serious biofilm-forming pathogens that cause complications ranging from minor to life-threatening infections. Methicillin-resistant *S. aureus* (MRSA) isolated from clinical environments has a high probability of forming biofilms. MRSA can cause a variety of problems ranging from skin infections to pneumonia, bloodstream infections, and sepsis. MRSA biofilm life cycle is believed to occur in four stages: the initial attachment of bacterial cells to a surface, formation of micro-colonies on the surface of interest, maturation of the micro-colonies into an established biofilm, and dispersal of the bacteria from the biofilm.

Biofilm in Food Industry

The demand for minimally processed, easily prepared and ready-to-eat 'fresh' food products poses major challenges for food safety and quality. Commonly, food contamination leads to spoilage and growth of pathogenic microorganisms. Contamination of food is common during slaughtering, processing, packaging and shipping stages of food processing. As food production becomes increasingly automated, the number of surfaces with which foods come into contact, and the potential for cross-contamination, increases. These surfaces are highly sensitive to microbial attachment and biofilm formation. It is imperative to food manufactures to design new approaches that inhibit microbial growth in food by inhibiting and eradicating biofilm formation while maintaining quality, freshness, and safety.

Host-Defense Peptides

Several Host-defense peptides (HDPs) were reported to prevent biofilm formation but only few were able to target existing mature biofilms. HDPs are produced by eukaryotes as part of the innate immune response to bacterial infection. The anti-microbial mechanism of action of HDP is attributed mainly to the disruption of bacterial membranes. They often display a characteristic selectivity, favoring an attack on prokaryotic membranes relative to eukaryotic membranes. HDPs are rich in hydrophobic residues which mediate disruptive interactions with the hydrophobic interior of the bacterial membrane lipid bilayer. The broad molecular diversity among HDPs suggests that their activity and selectivity is not tightly coupled to specific features of amino acid sequence or peptide conformation. This situation has encouraged the design of several types of random cationic polymers that mimic HDPs activity by displaying broad antimicrobial activity. Grinstaff and his co-workers showed that poly-amido-saccharide (PAS) prepared by a controlled anionic polymerization of β-lactam monomers derived from either glucose or galactose can inhibit biofilm formation (Dane et al., Chem Sci 2014, 5). Interestingly, it was shown previously that D-Amino acids, such as D-phenylalanine and D-tyrosine prevented biofilm development in *Staphylococcus aureus* and *Bacillus subtilis*.

Recently, a method to generate mixtures of random cationic peptides was developed by the inventor of the present invention and co-workers (Hayouka et al., *J Am Chem Soc*. 2013, 135: 32). A method of solid-phase peptide synthesis was employed using a mixture of two amino acids in each elongation step in a defined proportion. Using this method, synthesis of copolymers via n coupling steps generated $2^n$ sequences of random peptides with a defined composition and controlled chain length (Hayouka et al., ibid).

U.S. Pat. No. 6,172,038 discloses non-natural synthetic peptides comprising both L- and D-amino acid residues designated diastereomeric peptides with a net positive charge that is greater than +1. Some synthetic peptides consist of at least one hydrophobic amino acid and at least one positively charged amino acid, in which at least one of the amino acid residues is a D-amino acid.

U.S. Pat. No. 9,499,594 discloses methods for the prevention, control, disruption and treatment of bacterial biofilms with lysine, particularly lysine having capability to kill *Staphylococcal* bacteria, including drug resistant *Staphylococcus aureus*.

The inventor of the present invention and co-workers disclose that random-sequence peptide mixtures are capable of controlling and managing MRSA biofilms (Chem. Commun. April 2016, 52: 7102-7105).

The development of biofilms that allow for an aggregated cell bacteria to be increasingly antibiotic resistant as well as the general increasing resistance of bacteria to antimicrobial substances, necessitate the development of new methods for destroying and preventing biofilms.

Thus, there remains an unmet need for improved methods of preventing the formation of biofilm and/or eradicating biofilms.

SUMMARY OF THE INVENTION

The present invention provides methods for disrupting and/or preventing the formation of biofilms. In particular, the present invention provides methods for disrupting biofilms by applying mixtures comprising random-sequence peptides to the biofilm. The mixtures comprise hydrophobic and cationic amino acids. The length of the random-sequence peptides as well as the ratio of the total hydrophobic to cationic amino acids in the mixture is highly controlled and pre-defined.

The present invention is based in part on the unexpected findings that random-sequence peptide mixtures comprising hydrophobic and cationic amino acids, when contacted with a mature biofilm of antibiotic-resistant bacteria, were capable of disrupting the biofilm of the antibiotic-resistant bacteria as well as of killing these bacteria. The anti-biofilm activity of the random-sequence peptide mixtures was similar to the anti-biofilm activity of daptomycin, a lipopeptide antibiotic agent that is being used in the treatment of systemic and life-threatening infections caused by MRSA.

The negatively charged exopolysaccharides which form the biofilms are very effective in protecting microbial cells from positively charged antibacterial agents by restricting their permeation, possibly through binding. Unexpectedly, the random sequence peptide mixtures of the present invention which comprise cationic amino acids were found to penetrate an existing biofilm, disrupt its structure, and kill its embedded cells.

It is now disclosed that mixtures of homochiral or heterochiral 20-mer random-sequence peptides of phenylalanine and lysine ($^LF^LK$ or $^LF^DK$) at a 1:1 ratio prevented biofilm formations as well as disrupted mature bacterial biofilm. The heterochiral mixtures showed higher activity in biofilm disruption as compared to the homochiral mixtures. The homochiral or heterochiral mixtures were also shown to be highly potent in killing bacterial cells embedded within the biofilm biomass. The killing effect of the heterochiral mixtures was higher than that of the homochiral mixtures and was highly selective to bacterial cells because human red blood cells were essentially unaffected by these heterochiral mixtures. Moreover, the homochiral or heterochiral mixtures of phenylalanine and lysine ($^LF^LK$ or $^LF^DK$) showed an exceptional low cytotoxicity to human intestinal epithelial cell line, even at high concentrations.

It is further disclosed that the random-sequence peptide mixtures of the present invention were capable of penetrating into bacterial cells. Without being bound to any mechanism of action, the capability of the random-sequence peptides to penetrate into bacterial cells may indicate that the peptides may cause damage to the bacterial membrane and hence enhance the entry of the peptides into the bacterial cells.

Advantageously, the methods of the present invention are not associated with risks of acquired resistance as occur when one specific peptide sequence or a single antimicrobial agent are being used. In addition, the synthesis of random peptide mixtures is simple and cost-effective relative to the synthesis of specific peptide sequences.

Thus, the methods of disrupting biofilms, and specifically of antibiotic-resistant bacterial biofilms, of the present invention are highly efficient, selective, reduce the risk of developing bacterial resistance, and therefore are safe for human use.

According to one aspect, the present invention provides a pharmaceutical composition comprising a mixture of random-sequence peptides for use in treating or preventing a biofilm-associated infection in a subject, wherein the random-sequence peptides are of 3 to 50 amino acid residues in length, wherein said random-sequence peptides comprise hydrophobic and/or cationic amino acids, and wherein the ratio of the total hydrophobic and cationic amino acids in the mixture is between 10:1 and 1:10.

According to some embodiments, the biofilm-associated infection is caused by unicellular organisms. According to certain embodiments, the unicellular organism is selected from the group consisting of bacteria, fungi, yeast, and archaea.

According to some embodiments, the biofilm-associated infection is caused by gram-positive bacteria, gram-negative bacteria, or antibiotic resistant bacteria. According to additional embodiments, the bacteria are gram-positive bacteria. According to further embodiments, the bacteria are gram-negative bacteria.

According to some embodiments, the biofilm-associated infection is caused by bacteria selected from the group consisting of Staphylococcus, Bucillus subtilis, Streptococcus, Bacillus cereus, E. coli, Listeria, Salmonella, Pseudomonas, Acinetobacter baumannii, Klebsiella pneumoniae, Burkholderia cenocepacia, Helicobacter pylori, and Enterococcus. According to additional embodiments, the Staphylococcus or Streptococcus bacteria are selected from the group consisting of Staphylococcus aureus, Staphylococcus simulans, Streptococcus suis, Staphylococcus epidermidis, Streptococcus equi, Streptococcus agalactiae (GBS), Streptococcus pyogenes (GAS), Streptococcus sanguinis, Streptococcus gordonii, Streptococcus dysgalactiae, Group G Streptococcus, Group E Streptococcus, and Streptococcus pneumonia. Each possibility represents a separate embodiment of the invention.

According to some embodiments, the antibiotic resistant bacteria are selected from the group consisting of methicillin-resistant Staphylococcus aureus (MRSA), vancomycin resistant Staphylococcus aureus (VRSA), daptomycin-resistant Staphylococcus aureus (DRSA), linezolid-resistant Staphylococcus aureus (LRSA), Lactobacillus-MRS (LMRS), and vancomycin-resistant Enterococci (VRE). Each possibility represents a separate embodiment of the invention. According to specific embodiments, the bacteria are Bacillus subtilis. According to additional embodiments, the bacteria are Staphylococcus aureus. According to additional embodiments, the bacteria are MRSA. According to additional embodiments, the bacteria are Lactobacillus-MRS (LMRS). According to some embodiments, the bacteria are resistant to more than one antibiotic agent.

According to some embodiments, the mixture comprises heterochiral peptides. According to other embodiments, the mixture consists of homochiral peptides. According to some embodiments, the amino acids are all D-amino acids. According to additional embodiments, the amino acids are all L-amino acids. According to specific embodiments, if the hydrophobic amino acid is in the L-configuration, the cationic amino acid in the D-configuration. According to other embodiments, if the hydrophobic amino acid is in the D-configuration, the cationic amino acid in the L-configuration. According to yet further embodiments, the hydrophobic and cationic amino acids are in the L-configuration and/or D-configuration.

According to some embodiments, the hydrophobic amino acid is selected from the group consisting of phenylalanine, tryptophan, leucine, valine, alanine, isoleucine, glycine, and a combination thereof. Each possibility represents a separate embodiment of the invention. According to additional embodiments, the hydrophobic amino acid is a hydrophobic aromatic amino acid. According to certain embodiments, the hydrophobic aromatic amino acid is tryptophan or phenylalanine. According to one exemplary embodiment, the hydrophobic amino acid is phenylalanine. According to another exemplary embodiment, the hydrophobic amino acid is tryptophan.

According to some embodiments, the cationic amino acid is selected from the group consisting of lysine, arginine, histidine, ornithine, di-amino butyric acid (Dab), and a combination thereof. Each possibility represents a separate embodiment of the invention. According to an exemplary embodiment, the cationic amino acid is lysine.

According to some embodiments, the random-sequence peptide mixture consists of one species of a hydrophobic amino acid and one species of a cationic amino acid.

According to some embodiments, the hydrophobic amino acid is phenylalanine and the cationic amino acid is lysine. According to other embodiments, the hydrophobic amino acid is tryptophan and the cationic amino acid is lysine.

According to some embodiments, the ratio of the total hydrophobic and cationic amino acids in the mixture is about 5:1 to 1:5, alternatively about 3:1 to 1:3, and further alternatively about 1:1.

According to some embodiments, the random-sequence peptides are of 4, 5, 6, 7, 8, 9, 10, 11, 12, 13, 14, 15, 16, 17, 18, 19, 20, 25, 30 or 35 amino acid residues in length or any integer in between. Each possibility represents a separate embodiment of the invention.

According to some embodiments, the peptides within the mixture have identical number of amino acid residues in length, the number of residues ranges between 5 and 25, alternatively between 10 and 25, further alternatively between 15 and 25 residues in length. According to a certain embodiment, the peptides consist of 20 amino acid residues in length.

According to some embodiments, the biofilm-associated infection is selected from the group consisting of skin, oral, dental, genitourinary tract, and airways infections. According to certain embodiments, the biofilm-associated infection is selected from the group consisting of wound infection, Legionnaire's disease, middle-ear infection, acne, dental plaque infection, gingivitis, periodontitis, and cystic fibrosis.

According to some embodiments, the composition further comprises an anti-microbial agent. According to certain embodiments, the antimicrobial agent is an antibiotic agent. According to some embodiments, the antibiotic agent is selected from the group consisting of daptomycin, clindamycin, dicloxacillin, minocycline, nafcillin, oxacillin, ramoplanin, rifampin, triclosan, linezolid, penicillin, cephalosporin, and vancomycin. According to specific embodiments, the antibiotic agent is daptomycin.

According to an additional aspect, the present invention provides a method of treating or preventing a biofilm-associated infection in a subject comprising administering to the subject in need of such treatment a pharmaceutical composition comprising a mixture of random-sequence peptides of 3 to 50 amino acid residues in length, wherein the random-sequence peptides comprise hydrophobic and/or cationic amino acids, and wherein the ratio in the mixture of the total hydrophobic and cationic amino acids is between 10:1 and 1:10; and a pharmaceutically acceptable carrier.

According to another aspect, the present invention provides a method for preventing biofilm formation, the method comprises applying to a surface of an item a composition comprising an effective amount of a mixture of random-sequence peptides of 3 to 50 amino acid residues in length, said peptides comprise hydrophobic and/or cationic amino acids, wherein the ratio in the mixture of the total hydrophobic and cationic amino acids is between 10:1 and 1:10.

The biofilm and the peptides are as described hereinabove.

According to some embodiments, the item is a medical device, catheter or implant.

According to some embodiments, the medical device is selected from the group consisting of a cardiac rhythm management device (CRMD), a neurostimulator, a pulse generator, a drug pump or infusion device, a physiological monitoring device, or a textured or smooth breast implant.

According to some embodiments, the composition is immobilized to the surface of the medical device, catheter or implant.

According to some embodiments, the surface is coated with or covered by the composition according to the invention.

According to some embodiments, the item is commercial and industrial water systems.

According to an additional aspect, the present invention provides a method of inhibiting planktonic growth of antibiotic-resistant bacteria, the method comprises contacting antibiotic-resistant bacteria with a composition comprising a mixture of random-sequence peptides of 3 to 50 amino acid residues in length, wherein the peptides comprise hydrophobic and/or cationic amino acids, and wherein the ratio in the mixture of the total hydrophobic and cationic amino acids is between 10:1 and 1:10; and a pharmaceutically acceptable carrier.

The mixture and the peptides are as described hereinabove.

According to some embodiments, the bacteria are methicillin-resistant *Staphylococcus aureus* (MRSA).

Other objects, features and advantages of the present invention will become clear from the following description and drawings.

BRIEF DESCRIPTION OF THE FIGURES

FIG. 7A shows MRSA cells, not treated with the peptides. FIGS. 7B and 7C show MRSA cells treated with Fl'-$^L$F$^L$K and Fl'-$^L$F$^D$K, respectively.

DETAILED DESCRIPTION OF THE INVENTION

Figure 1:
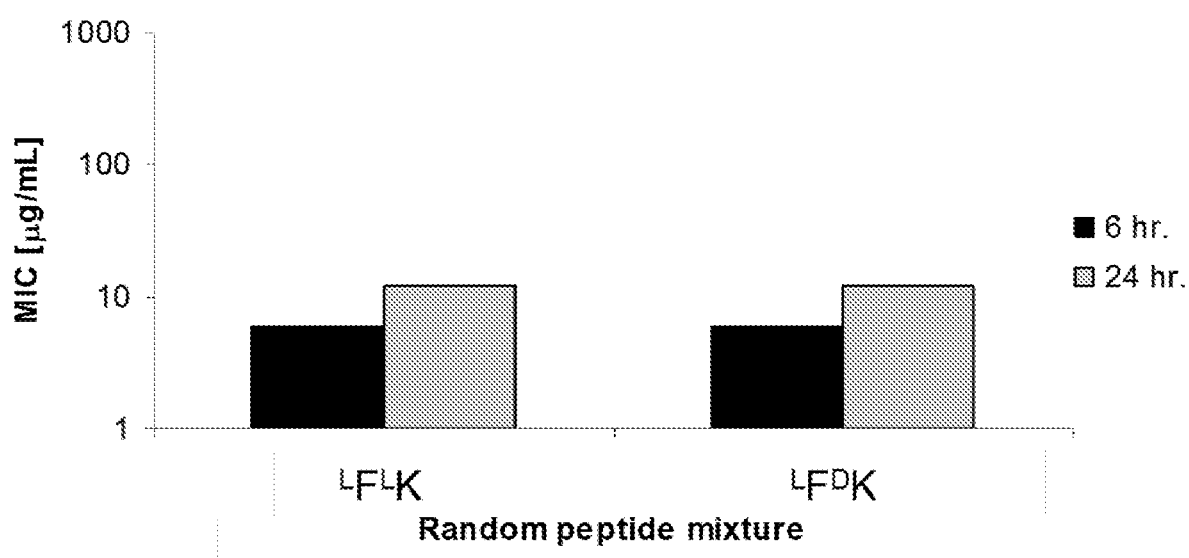
FIG. 1 shows the effect of random-sequence peptide mixtures on the growth of methicillin-resistant *Staphylococcus aureus* (MRSA). Clinically isolated strain of MRSA was treated with random sequence 20-mer phenylalanine-lysine peptide mixtures (homochiral $^LF^LK$ or heterochiral $^LF^DK$). Growth-inhibitory activities were measured after incubation of 6 hr or 24 hr.

The present invention provides pharmaceutical compositions comprising random-sequence synthetic peptide mixtures for use in treating or preventing biofilm-associated infections and/or for use in disrupting biofilm and/or for use in killing bacteria embedded in a biofilm and/or for use in preventing formation of biofilm, in a subject in need of such treatment. The present invention further provides random-sequence synthetic peptide mixtures for use in preventing biofilm formation on a surface of medical devices, on food processing surfaces, or on commercial and industrial water systems. The mixture comprises random sequence peptides of 3 to 50 amino acid residues in length, wherein the peptides comprise hydrophobic and/or cationic amino acids, and wherein the ratio in the mixture of the total hydrophobic to cationic amino acids is highly controlled and pre-defined.

Random-sequence peptide mixtures are significantly advantageous compared to anti-biofilm specific peptide sequences for two reasons: (1) the synthesis of random-sequence peptide mixtures is easy and cost-effective relative to the synthesis of specific peptide sequences; and (2) the mixtures contain many peptides with different amino acid sequences, and as such can be considered to be a cocktail of anti-biofilm agents which reduce or even eliminate the risks of acquired antibiotic resistance in bacteria.

Advantageously, it is now disclosed that mixtures of synthetic random sequence peptides comprising hydrophobic and cationic amino acids are highly efficient in preventing biofilm formation, in eradicating an existing or mature biofilm, and in killing bacteria embedded or associated with biofilms. The present invention teaches that specific amino acid sequences of antimicrobial peptides are not essential for preventing biofilm formation, for eradicating an existing biofilm, and for killing bacteria associated with biofilm.

The inventors of the present invention showed that mixtures of random sequence peptides of hydrophobic amino acids and cationic amino acids, e.g., phenylalanine-lysine, tryptophan-lysine, and leucine-lysine, showed high anti-biofilm activity. However, higher anti-biofilm activity was observed with peptide mixtures of hydrophobic aromatic amino acids and cationic amino acids, e.g., a phenylalanine-lysine mixture, in some experimental conditions. In addition, heterochiral mixtures of hydrophobic aromatic amino acids and cationic amino acids showed higher anti-biofilm activity than homochiral mixtures, and such heterochiral mixtures were found to be essentially non-toxic to human cells.

The term "biofilm" refers to a population of microorganisms, such as bacteria, growing on a surface, wherein the bacteria are encased in a matrix generally composed of polysaccharides, proteins and nucleic acids. In this state, bacteria are less susceptible to both phagocytes and antibiotics. The term "biofilm" is further intended to include biological films that develop and persist at interfaces in aqueous environments.

The terms "disrupting biofilm" and "eradicating biofilm" are used herein interchangeably and are defined as the ability of the mixtures as defined in the present invention to degrade an existing or mature biofilm and/or to inhibit, prevent, or reduce the formation of a biofilm in vitro as well as in vivo and/or to kill microorganisms embedded or associated with biofilms.

The terms "preventing biofilm formation" or "reducing biofilm formation" are used herein interchangeably and refer to the ability of the mixtures disclosed herein to avert or reduce the formation of a biofilm by microorganisms. According to some embodiments, preventing biofilm formation means inhibiting bacterial attachment to a surface. Additionally or alternatively, preventing biofilm formation means killing the biofilm-forming bacteria.

The term "mixture" as used herein refers to at least two different random-sequence peptides as discloses herein, preferably to a plurality of random-sequence peptides. According to the invention, the mixture of random-sequence peptides comprises or consists of cationic amino acids and hydrophobic amino acids. The mixture can be mixed with another anti-microbial agent.

The term "random-sequence peptide" as used herein refers to a peptide, the amino acid sequence of which is different from the amino acid sequence of at least one peptide in the mixture. According to some embodiments, the mixture can have up to $2^n$ amino acid sequences, wherein n defines the number of coupling steps in the peptide synthesis, if one species of a cationic amino acid residue and one species of a hydrophobic amino acid residue are present both in L-configuration or D-configuration. According to further embodiments, the mixture can have up to $4^n$ amino acid sequences, wherein n defines the number of coupling steps in the peptide synthesis, if one species of a cationic amino acid residue and one species of a hydrophobic amino acid residue are present in L-configuration and D-configuration. Thus, the number of random-sequence peptides in a mixture is dictated by the length of the peptides synthesized, the various species of amino acids, and the configuration of the amino acids.

According to the invention, the random-sequence peptides comprise or consist of hydrophobic and/or cationic amino acids. According to some embodiments of the invention, one or more peptides in the mixture, preferably 10% or less, such as less than 1% of the peptides in the mixture, comprise or consist of hydrophobic amino acids but are devoid of cationic amino acids, one or more peptides in the mixture, preferably about 10% or less, such as less than 1% of the peptides in the mixture, comprise or consist of cationic amino acids but are devoid of hydrophobic amino acids, and at least about 80% of the peptides in the mixture, alternatively at least about 90%, 95%, or preferably at least about 99% of the peptides in the mixture comprise or consist of a combination of cationic and hydrophobic amino acids. According to a certain embodiment, the peptides of the mixture comprise or consist of a combination of hydrophobic and cationic amino acid residues.

The term a "cationic amino acid" refers to a positively charged amino acid, also known as a basic amino acid.

The term "ratio" as applied to the amino acids within a mixture refers to the ratio between different classes of amino acids which constitute the peptides present in the mixture.

For example, "a ratio in the mixture of the total hydrophobic and cationic amino acids" refers to the number of all hydrophobic amino acids present in or constitute the peptides of the mixture relative to the number of all cationic amino acids present in or constitute the peptides of the mixture.

The term "stereoisomeric forms" refers to the L- or D-configuration of amino acids. Unless otherwise mentioned or indicated, the amino acids are in L configuration.

The term "homochiral" as used herein refers to amino acids having the same configuration (i.e., L-configuration or D-configuration).

The term "heterochiral" as used herein refers to amino acids having different configurations, i.e., one is in the L-configuration and the other is in the D-configuration.

The term "heterochiral mixture" as used herein refers to a mixture comprising random-sequence peptides; at least one of the peptides consists of amino acids in the L-configuration and amino acids in the D-configuration. Preferably, a heterochiral mixture comprises a plurality of peptides consisting of amino acids in the L-configuration and amino acids in the D-amino configuration.

The term "homochiral mixture" as used herein refers to a mixture comprising random-sequence peptides, wherein all the peptides consist of amino acids in the L-configuration or in the D-configuration.

The singular forms "a", "an" and "the" include corresponding plural references unless the context clearly dictates otherwise.

As used herein, the term "about" means plus or minus 10% of the numerical value indicated.

According to some embodiments, disrupting the biofilm is characterized by reducing the biofilm biomass by at least 10%, 20%, 30%, 40%, 50%, 60%, 70%, 80%, 90%, or 95% compared to a non-treated biofilm. Each possibility represents a separate embodiment of the invention.

According to some embodiments, the biofilm formation is reduced by at least 20%, 30%, 40%, 50%, 60%, 70%, 80%, 90%, or 95% compared to a non-treated site. Each possibility represents a separate embodiment of the invention.

According to some embodiments, disrupting the biofilm is characterized by killing at least 20%, 30%, 40%, 50%, 60%, 70%, 80%, 90%, or 95% of the bacterial population in the biofilm.

Cationic amino acids as used herein are selected from cationic or positively charged amino acids known in the art. Positively charged amino acids include, but are not limited to, lysine, arginine, and histidine. Hydrophobic amino acids as used herein are selected from hydrophobic amino acids known in the art. Hydrophobic amino acids include, but are not limited to, phenylalanine, tryptophan, leucine, isoleucine, glycine, alanine, and valine. According to some embodiments, the hydrophobic amino acid is a hydrophobic aromatic amino acid. According to certain embodiments, the hydrophobic aromatic amino acid is phenylalanine or tryptophan. The peptides of the present invention comprise L-amino acids, D-amino acids, or a combination thereof. The amino acids may also be selected from non-protein amino acids, such as, for example, ornithine. The amino acids of the invention can be non-natural amino acids such as, for example, n-methylated amino acids, γ-amino acids, and ring-substituted phenylalanine.

The peptides of the present invention can further comprise additional amino acid residues, such as polar or uncharged amino acid residues, for example, asparagine and/or serine, as long as the ratio between the total r cationic amino acid residues and the total hydrophobic amino acid residues in the mixture is maintained between about 10:1 to 1:10, alternatively about 5:1 to 1:5, alternatively about 3:1 to 1:3, and preferably about 1:1.

According to some embodiments, the random-sequence peptides in the mixture comprise or consist of hydrophobic amino acid residues, cationic amino acid residues, or a combination thereof. According to additional embodiments, the random-sequence peptides comprise or consist of one species of a hydrophobic amino acid residue and one species of cationic amino acid residue. According to exemplary embodiments, the random-sequence peptide mixture consists of phenylalanine and lysine, tryptophan and lysine, or leucine and lysine. According to a certain embodiment, the random-sequence peptide mixture consists of phenylalanine and lysine, or tryptophan and lysine.

The random-sequence peptide mixtures of the present invention can be synthesized by a solid phase peptide synthesis method as described herein below. The random-sequence peptide mixtures can also be synthesized by other solid phase peptide synthesis methods, such as the solid-phase mix-and-split combinatorial synthesis method, as known in the art.

Pharmaceutical Compositions

The present invention provides pharmaceutical compositions comprising a therapeutically effective amount of random-sequence synthetic peptide mixtures of the invention and a pharmaceutically acceptable carrier or diluent, for use in disrupting biofilm or for treating or preventing biofilm-associated infection in a subject.

The term "pharmaceutical composition" as used herein refers to a composition comprising at least one pharmaceutically active ingredient.

The pharmaceutical compositions of the present invention comprise a pharmaceutically acceptable carrier. The term "carrier" refers to a diluent or vehicle with which the therapeutic compound is administered. Carrier(s) are "acceptable" in the sense of being compatible with the other ingredients of the composition and not deleterious to the recipient thereof. Such pharmaceutical carriers can be sterile liquids, such as water; oils, including those of petroleum, animal, vegetable or synthetic origin, such as peanut oil, soybean oil, mineral oil, sesame oil and the like; polyethylene glycols; glycerin; propylene glycol; or other synthetic solvents. For injectable solutions, water is a preferred carrier when the pharmaceutical composition is administered intravenously. Saline solutions and aqueous dextrose and glycerol solutions can also be employed as liquid carriers for injectable solutions.

The pharmaceutical composition can further comprise a surfactant. According to some embodiments, the surfactant is a nonionic surfactant. Nonionic surfactants include, but are not limited to, sorbitan fatty acid esters, polyoxysorbitan fatty acid esters, polyoxyalkylene higher alcohol ethers, and polyoxyalkylene higher alcohol esters. Thus, nonionic surfactants include polyoxyethylene sorbitol esters such as polysorbate 80 (TWEEN® 80), polysorbate 60 (TWEEN® 60) and polysorbate 20 (TWEEN® 20), Tyloxapol; polyoxyethylene isooctylphenyl ethers such as Triton X-100, polyoxyethylene nonylphenyl ethers such as NP-40, polyoxyethylene dodecyl ethers such as Brij 58, octyl glucoside, and alkyl maltoside such as n-dodecyl-beta-D-maltoside; Poloxamer 4070; Poloxamer 188; and polyoxyl 40 stearate. Each possibility is a separate embodiment of the invention. TWEEN® and Poloxamer surfactants are preferred because they are FDA approved for human use.

The pharmaceutical compositions of the present invention can be formulated as a liquid. The liquid composition can be stored as is or can be stored in a frozen state, or in a dried form for later reconstitution into a liquid form or other form suitable for administration to a subject.

The compositions may be suitably formulated for subcutaneous, intramuscular, intraperitoneal or intravenous administration and comprise sterile aqueous solutions, which are preferably isotonic. Such formulations are typically prepared by dissolving solid active ingredients in water containing physiologically compatible substances such as sodium chloride, glycine, and the like, and having a buffered pH compatible with physiological conditions to produce an aqueous solution, and rendering said solution sterile. These may be prepared in unit or multi-dose containers, for example, sealed ampoules or vials.

The compositions may incorporate a stabilizer, such as for example polyethylene glycol, proteins, saccharides (for example, trehalose), amino acids, inorganic acids and admixtures thereof. Stabilizers are used in aqueous solutions at the appropriate concentration and pH. The pH of the pharmaceutical composition of the present invention is adjusted to be within the range of 5.0-9.0, preferably within the range of 6-8.

According to some embodiments, the compositions of the invention may be formulated for oral administration in liquid solutions, emulsions, suspensions, tablets, dragees, capsules, powder, and the like. The pharmaceutically-acceptable carriers suitable for preparation of such compositions are well known in the art. Proteins or peptides that are orally administered need to be protected as to avoid digestion by the gastrointestinal system.

The mixtures of the invention can be coated with enteric coating layer(s) as to protect the peptides from digestion. Enteric coating layer(s) may be applied using standard coating techniques. The enteric coating materials may be dissolved or dispersed in organic or aqueous solvents and may include one or more of the following materials: methacrylic acid copolymers, shellac, hydroxypropylmethylcellulose phthalate, polyvinyl acetate phthalate, hydroxypropylmethylcellulose, carboxymethylethylcellulose, cellulose acetate phthalate or other suitable enteric coating polymer(s). The pH at which the enteric coat will dissolve can be controlled by the polymers, combination and ratio of selected polymers, and/or their side groups. For example, dissolution characteristics of the polymer film can be altered by the ratio of free carboxyl groups to ester groups. Enteric coating layers also contain pharmaceutically acceptable plasticizers such as triethyl citrate, dibutyl phthalate, triacetin, polyethylene glycols, polysorbates or other plasticizers. Additives such as dispersants, colorants, anti-adhering and anti-foaming agents may also be included.

The compositions of the invention may be formulated as controlled release preparations which may be achieved through the use of a polymer to complex or absorb the proteins of the invention. Appropriate polymers for controlled release formulations include, for example, polyester, polyamino acids, polyvinyl, pyrrolidone, poly (lactic acid), ethylenevinylacetate, ethylene vinylacetate copolymers, and cellulose derivatives such as methylcellulose. Alternatively, it is possible to entrap the proteins of the invention in microcapsules prepared, for example, by coacervation techniques or by interfacial polymerization, for example, hydroxymethylcellulose or gelatin-microcapsules and poly (methylmethacylate) microcapsules, respectively, or in colloidal drug delivery systems, for example, liposomes, albumin microspheres, and nanoparticles.

The compositions of the present invention can further comprise an additional therapeutic agent.

According to some embodiments, the therapeutic agent is an antibiotic agent. The antibiotic agents include, but are not limited to, β-lactams, aminoglycosides, fluoroquinolones, macrolides, novobiocin, rifampicin, oxazolidinones, fusidic acid, mupirocin, pleuromutilins, daptomycin, vancomycin, tetracyclines, sulfonamides, chloramphenicol, trimetoprim, fosfomycin, cycloserine, polymyxin, azithromycin, clarithromycin, dirithromycin, erythromycin, troleandomycin, roxithromycin, spiramycin, aztreonam, imipenem, meropenem, ertapenem, doripenem, panipenem/betamipron, biapenem, PZ-601, cefixime, cefdinir, cefditoren, cefoperazone, cefotaxime, cefpodoxime, ceftazidime, ceftibuten, ceftizoxime, ceftriaxone, cefepime, demeclocycline, doxycycline, minocycline, oxytetracycline, tetracycline, bacitracin, colistin, ciprofloxacin, enoxacin, gatifloxacin, levofloxacin, lomefloxacin, moxifloxacin, norfloxacin, ofloxacin, and trovafloxacin.

The antibiotic agent can be one or more of the known host-defense peptides (HDPs).

According to some embodiments, the composition of the invention improves the activity of the antibiotic agent. Improving the efficacy of the antibiotic agent includes any aspect of improving or enhancing the effect of the antibiotic agent, e.g. so that the anti-biofilm effect of the antibiotic agent is increased or enhanced in any way over the effect of the antibiotic agent seen in the absence of the mixtures according to the invention. This may be seen, for example, in a stronger effect of the antibiotic agent in inhibiting growth of the bacteria, requiring less antibiotics to achieve the same effect seen in the absence of the mixtures according to the invention, or an increased effectiveness seen as increased speed or rate of action, a biofilm eradicating effect being seen in less time than in the absence of said mixtures.

According to further embodiments, the therapeutic agent is an antiviral drug or an anti-fungal drug.

Therapeutic Uses of Random Sequence Peptide Mixtures

The present invention provides uses of the pharmaceutical compositions comprising a therapeutically effective amount of random sequence peptide mixtures of the invention for disrupting biofilm in a subject in need.

According to an aspect, the present invention provides a method for treating a biofilm-associated infection in a subject comprising administering to the subject a pharmaceutical composition comprising a therapeutically effective amount of a mixture of random-sequence peptides according to the invention and a pharmaceutically acceptable carrier.

Biofilm-forming bacteria, such as *staphylococci, Staphylococcus aureus, Enterococcus faecalis, Streptococcus* spp., *Escherichia coli, Klebsiella pneumoniae, Acinetobacter* spp., *Proteus mirabilis, Pseudomonas aeruginsa* and *Candida* spp, *Staphyloccus saprophyticus, Staphyloccocus xylosus, Staphyloccocus lugdunensis, Staphyloccocus schleiferi, Stapylococcus caprae, Staphylococcus epidermidis, Staphylococcus hominis, Staphylococcus saprophyticus, Staphylococcus warneri*, MRSA, *Enterococcus faecalis* (including Vancomycin-resistant enterococcus VRE), *Proprionibacterium acnes, Bacillus cereus, Bacillus subtilis, Listeria monocytogenes, Streptococcus pyrogenes, Streptococcus salivarius*, or *Streptococcus mutans* are associated with a broad spectrum of biofilm-associated infections, particularly of nosocomial infections. The bacterial microorganisms form biofilm to be protected against the immune system. The mixtures of the inventions are useful in killing the biofilm forming bacteria as well as other bacteria that may be protected by the biofilm.

The methods of the invention are useful in treating any biofilm-associated infection. The infection can be, for example, in the oral cavity, the reproductive tract, the urinary tract, the respiratory tract, the gastrointestinal tract, the peritoneum, the middle ear, the prostate, vascular intima, the eye, including the conjunctiva or corneal tissue, in the lung tissue, heart valves, skin, scalp, nails, in wounds; or in the blood.

Typical bacterial infections associated with biofilms in humans are: wound infections, in particular wounds associated with diabetes mellitus, tonsillitis, osteomyelitis, bacterial endocarditis, sinusitis, infections of the cornea, urinary tract infection, infection of the biliary tract, infectious kidney stones, urethritis, prostatitis, catheter infections, gastrointestinal infections, Legionnaire's disease, middle-ear infections, dental plaques, gingivitis, periodontitis, cystic fibrosis, and infections of permanent indwelling devices such as joint prostheses, and heart valves.

Skin infections include, but are not limited to, cellulitis, folliculitis, impetigo, and boils.

The infection may be acute, or alternatively chronic, e.g. an infection that has persisted for at least 5 or at least 10 days, particularly at least 20 days, more particularly at least 30 days, most particularly at least 40 days.

The biofilm-associated infection can occur in any subject but some subjects will be more susceptible to infection than others. Subjects who are susceptible to these infections include, but are not limited to, subjects whose epithelial and/or endothelial barrier is weakened or compromised, subjects whose secretion-based defenses to microbial infection have been abrogated, disrupted, or weakened, and subjects who are immunocompromised, immunodeficient or immunosuppressed (i.e., a subject in whom any part of the immune response, or an immune activity is reduced or impaired, whether due to disease or clinical intervention or other treatment, or in any way).

The term "therapeutically effective amount" as used herein refers to an amount of the active agent, namely a mixture according to the invention that is sufficient to treat, alleviate, and/or inhibit one or more symptoms of a disease or disorder associated with the formation of biofilm in an individual. The therapeutically effective amount will vary depending on the active agent, formulation, the disease and its severity and the age, weight, physical condition and responsiveness of the subject to be treated.

The dosage and route of administration used in a method of disrupting a biofilm in a subject according to the present invention depends on the specific disease/site of infection to be treated.

As used herein, the term "treating" means remedial treatment, and encompasses the terms "reducing", "suppressing", "ameliorating" and "inhibiting", which have their commonly understood meaning of decreasing or arresting an infection.

The pharmaceutical composition of the invention may be administered by any suitable administration route, such as by parenteral or by oral administration route. According to some embodiments, the route of administration is via parenteral injection. According to additional embodiments, the parenteral route of administration is selected from the group consisting of subcutaneous, intramuscular, intradermal, intraperitoneal, intravenous, intraarterial, and intrathecal. The compositions of the invention can be administered locally.

The pharmaceutical composition of the present invention can be administered once a week, twice a week, three times a week for a period of at least two weeks, three weeks, four weeks, 2 months, 3 months, 4 months, 5 months, 6 months, or 12 months or any integer in between as required so as to disrupt or prevent the formation of biofilm Each possibility represents a separate embodiment of the invention.

The dosage of random sequence peptide mixture administered can range from about 10 ng/kg to about 500 mg/kg of the subject's weight or any integer in between. According to some embodiments, the dosage of random sequence peptide mixtures administered ranges from about 20 ng/kg to about 20 mg/kg of the subject's weight. According to some embodiments, the dosage of pharmaceutical composition comprising the mixture of the invention, when administered intravenously, ranges from about 3 mg/kg to 10 mg/kg daily for 2-6 weeks.

According to some embodiments, the method of the present invention comprises a combination therapy wherein a therapeutic agent formulated in a separate composition can be administered before, simultaneously, or after the compositions of the present invention or in alternate schedule.

Other Uses of Random-Sequence Peptide Mixtures

According to an additional aspect, the present invention provides a method for preventing the formation of biofilm on a medical device, catheter or implant comprising contacting the medical device, catheter or implant with a composition comprising a mixture of random-sequence peptides according to the invention.

According to some embodiments, the medical device includes, but is not limited to, a cardiac rhythm management device (CRMD), a neurostimulator, a pulse generator, a drug pump or infusion device, a physiological monitoring device, and a textured or smooth breast implant.

Medical devices include, but are not limited to, disposable or permanent or indwelling catheters, (e.g., central venous catheters, dialysis catheters, long-term tunneled central venous catheters, short-term central venous catheters, peripherally inserted central catheters, peripheral venous catheters, pulmonary artery Swan-Ganz catheters, urinary catheters, and peritoneal catheters), long-term urinary devices, tissue bonding urinary devices, vascular grafts, vascular catheter ports, wound drain tubes, ventricular catheters, hydrocephalus shunts, heart valves, heart assist devices (e.g., left ventricular assist devices), pacemaker capsules, pulmonary ventilators, incontinence devices, penile implants, small or temporary joint replacements, urinary dilator, cannulas, elastomers, surgical instruments, dental instruments, tubings, such as intravenous tubes, breathing tubes, dental water lines, dental drain tubes, feeding tubes, fabrics, paper, adhesives (e.g., hydrogel adhesives), bandages, orthopedic implants, and any other device used in the medical field.

Medical devices also include any device which may be inserted or implanted into a human or other animal, or placed at the insertion or implantation site such as the skin near the insertion or implantation site, and which include at least one surface which is susceptible to colonization by biofilm embedded microorganisms.

The compositions comprising the mixture of the invention can be used as a sanitizing agent. Said sanitizing agent can be used, for example, before or after surgery.

The composition can be further used as a disinfectant e.g., in human organ surgery, in dental surgery, in animal surgery. For that aim, the mixtures of the invention can be prepared in a composition in the form of e.g., a spray, a fluid, a powder, a gel, or as an ingredient of a wet wipe or a disinfection sheet product. Said compositions may additionally comprise suitable carrier, additives, diluting agents and/or excipients for its respective use and form.

According to another aspect, the present invention provides an item, such as, a medical device, catheter or implant, coated with or covered by the composition of the present invention. The coating of the composition comprising the mixture of random-sequence peptides can be in some embodiments via covalent binding so that the peptides are immobilized to the surface of the item.

The surface can be made of any material. For example it may be metal, e.g., aluminum, steel, stainless steel, chrome, titanium, iron, alloys thereof, and the like. The surface can also be plastic, for example, polyolefin (e.g., polyethylene, (Ultra-High Molecular Weight) polyethylene, polypropylene, polystyrene, poly(meth)acrylate, acrylonitrile, butadiene, ABS, acrylonitrile butadiene, etc.), polyester (e.g., polyethylene terephthalate, etc.), and polyamide (e.g., nylon), combinations thereof, and the like. Other examples include acetal copolymer, polyphenylsulfone, polysulfone, polythermide, polycarbonate, polyetheretherketone, polyvinylidene fluoride, poly(methyl methacrylate) and poly(tetrafluoroethylene). The surface can also be ceramic, porcelain, gold, and the like.

The compositions comprising a mixture of random-sequence peptides according to the invention can be used for the prevention of Gram-negative and/or Gram-positive bacterial contamination associated with bacterial biofilm of food stuff, of food processing equipment, of food processing plants, and of water systems.

Surfaces exposed to microbial contact or contamination include in particular any part of: food or drink processing, preparation, storage or dispensing machinery or equipment, air conditioning apparatus, industrial machinery, e.g. in chemical or biotechnological processing plants, and storage tanks. Any apparatus or equipment for carrying or transporting or delivering materials is susceptible to microbial contamination. Such surfaces will include particularly pipes (which term is used broadly herein to include any conduit or line). Representative inanimate or abiotic surfaces include, but are not limited to, food processing, storage, dispensing or preparation equipment or surfaces, tanks, conveyors, floors, drains, coolers, freezers, equipment surfaces, walls, valves, belts, pipes, air conditioning conduits, cooling apparatus, food or drink dispensing lines, heat exchangers, boat hulls or any part of a boat's structure that is exposed to water, dental waterlines, oil drilling conduits, contact lenses and storage cases. Surfaces of water systems exposed to microbial contact or contamination include in particular any part of: pipes and tubes, valves, filters, reservoirs, basins, and any part in water irrigation systems.

According to some embodiments, the composition can be a cosmetic composition. For example, the cosmetic composition can be used for eliminating, reducing and/or preventing biofilm-associated bacterial growth on a human skin.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Materials and Methods
(i) Chemicals
Fmoc-protected L/D α-amino acids with acid-labile side-chain protecting groups were purchased from Novabiochem. N-hydroxybenzotriazole (HOBt), N,N-dimethylformamide (DMF), and N,N-diisopropylethylamine (DIEA) were purchased from Sigma-Aldrich. 2-(1H-Benzotriazole-1-yl)-1,1,3,3-tetramethyluronium hexafluorophosphate (HBTU) was purchased from Anaspec. Dehydrated LB culture medium (244610) was obtained from BD (Franklin Lakes, N.J.). All other chemicals were purchased from Sigma Aldrich and used without purification.

(ii) Synthesis of Random-Sequence Peptide Mixtures
Random peptide mixtures were synthesized using microwave irradiation on Rink Amide resin (Substitution 0.2 mmol/gr, 25 μmol) in Alltech filter tubes. Coupling reactions were conducted with binary combinations of L/D-protected amino acids, with a freshly prepared stock solution that contained the protected amino acids in 1:1 molar ration, which was used for each coupling step. Before each coupling step, an aliquot containing 4 equiv. (100 μmol) of the amino acid mixture was activated with 4 equiv. of HBTU, 4 equiv. of HOBt, and 8 equiv. of DIEA, in DMF. After the activated amino acid solution was added to the solid-phase synthesis resin, the reaction mixture was heated to 70° C. in a MARS V multimode microwave (2 minute ramp to 70° C., 4 minute hold 70° C.) with stirring. Fmoc deprotection reactions used 20% piperidine in DMF. Reaction solutions were heated to 80° C. in the microwave (2 minute ramp to 80° C., 2 minute hold 80° C.) with stirring. After each coupling/deprotection cycle the resin was washed 3 times with DMF. Upon completion of the synthesis, the peptide mixture was cleaved from the resin by stirring the resin in a solution containing 95% trifluoroacetic acid (TFA), 2.5% water, and 2.5% triisopropylsilane for 3 hours. The peptide mixture was precipitated from the TFA solution by addition of cold ether. The precipitated peptide mixture was collected by centrifugation. Ether was removed, and the pellet was dried under a stream of nitrogen, frozen in dry ice and lyophilized.

(iii) Bacterial Growth Inhibition Assays (MIC)
Assays were performed as previously reported (Hayouka, Z. et at, J Am Chem Soc 2013, 135: 32). The bacteria used in these assays was methicillin resistant *Staphylococcus aureus* 1206 (Weisblum, B. et al., J Bacteriol, 1969, 98, 447). Antibacterial activities were determined in sterile 96-well plates (BD Falcon 353072 tissue culture plates). Bacterial cells were grown overnight at 37° C. on agar, after which a bacterial suspension of approximately $2\times10^6$ CFU/mL in Luria Bertani (LB) growth medium was prepared. Samples (50 μL) of this suspension were added to 50 μL of medium containing the random-sequence peptide mixture in 2-fold serial dilutions for a total volume of 100 μL in each well. The plates were then incubated at 37° C. for 6 or 24 hours. Bacterial growth was determined by measuring the optical density (OD) at 650 nm (Tecan Safire plate reader). The positive control was OD without the addition of peptide mixture. The minimum inhibitory concentration (MIC) is defined as the lowest concentration at which complete inhibition of bacterial growth was observed (no increase in OD over the course of the experiment).

(iv) Biofilm Assay
Clinical isolate strain of *S. aureus* (1206) was used. Bacterial cells were grown overnight at 37° C. on agar, after which a bacterial suspension of approximately $2\times10^6$ CFU/mL in LB medium was prepared. 100 μL of the bacterial suspension was then inoculated in several wells of a 96 well plate and incubated overnight at 37° C. The supernatant liquid was discarded and the wells were washed with milli-Q water three times. 1004, of LB medium containing the random peptide mixture or antibiotic in 2-fold serial dilutions were added to the wells containing the biofilm and the plates were incubated overnight at 37° C. (in the biofilm biomass assay for daptomycin, all antibiotic/biofilm mixture at varied daptomycin concentration contained 1 mM CaCl$_2$). The supernatant liquid was discarded. The wells were then washed with milli-Q water three times.

(v) Crystal Violet Assay for Biomass Quantification

The wells were treated with 125 4, of 0.1% crystal violet and incubated for 15 min at 37° C. Excess crystal violet was washed off thoroughly with milli-Q water three times. 125 4, of 30% acetic acid was added to each well and the solution was transferred to a new 96-well plate, and absorbance was measured at 550 nm (Tecan Safire plate reader) using 30% acetic acid in water as blank. The results were expressed as a percentage of biomass in the control biofilm, which was grown without any treatment.

(v) XTT Assay for Cell Viability within Biofilm

Cell viability in the biofilms was quantified after incubation with random-sequence mixture or antibiotic for 24 hours by an XTT assay. XTT (1 mg/mL) and phenazine methosulfate in the ratio 3:1 were freshly prepared in 1×PBS buffer. Following the washing step of the biofilm after treatment, 100 µL of this solution was added to the wells and the plates were incubated at 37° C. for 3 hours in the dark. An aliquot of 90 µL was taken and transferred to a 96-well plate and OD was measured at 490 nm (Tecan Safire plate reader) using the XTT solution as blank. The results were expressed as a percentage of cell viability relative to the control biofilm without any treatment.

Example 1

Effect of Random Sequence Peptide Mixtures on the Growth of Methicillin-Resistant *Staphylococcus aureus*

The ability of the random-sequence peptide mixture to inhibit the growth of planktonic MRSA cells after 6 h or 24 h was examined. As shown in FIG. 1, 20-mer random-sequence peptide mixtures of 1:1 homochiral or heterochiral phenylalanine-lysine ($^LF^LK$ or $^LF^DK$) inhibited the growth of planktonic MRSA at a very low concentration. The Minimal Inhibition Concentration (MIC) was 6 µg/mL for 6 h incubation and 12 µg/mL for 24 h incubation.

Example 2

Random Sequence Peptide Mixtures Disrupt Biofilms

Figure 2:
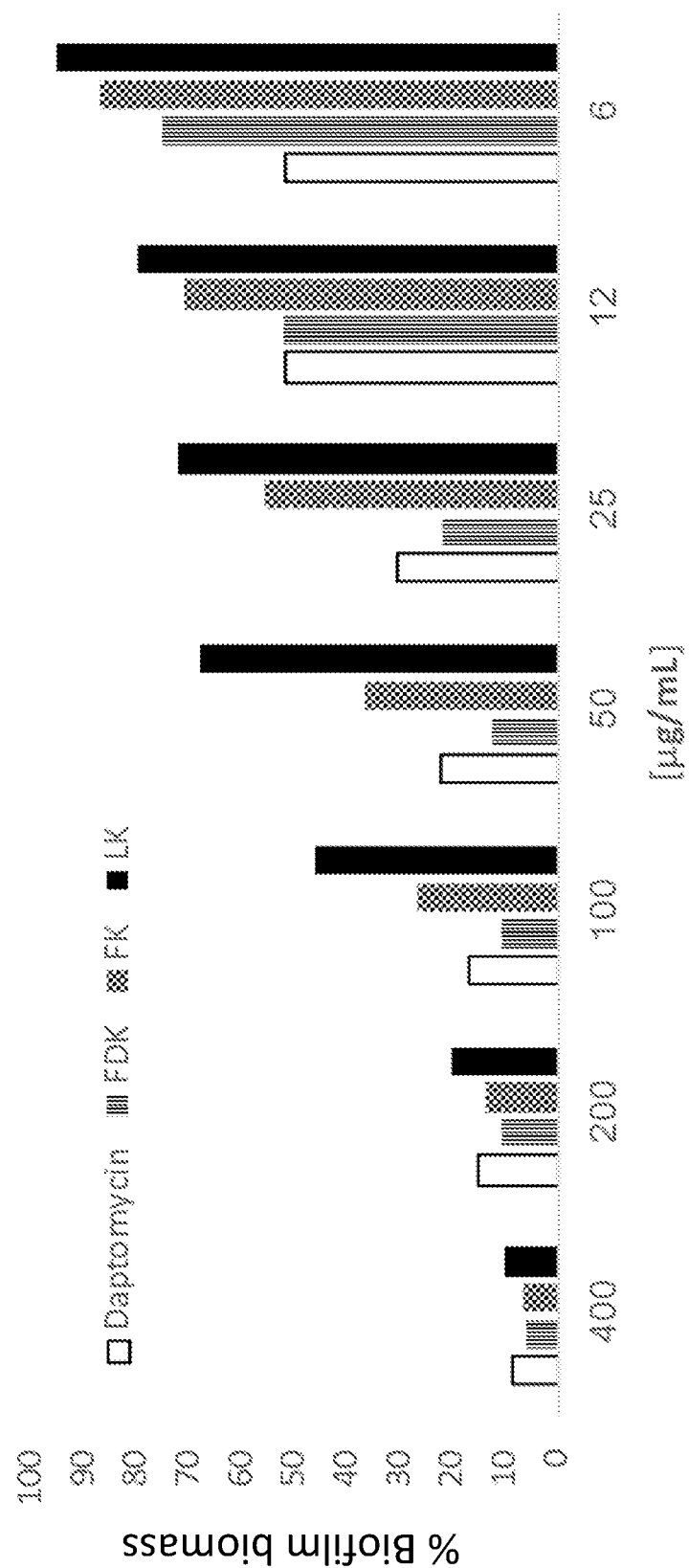
FIG. 2 shows the effect of random sequence peptide mixtures on MRSA biofilm degradation. Random sequence 20-mer phenylalanine-lysine peptide mixtures (homochiral $^LF^LK$ or heterochiral $^LF^DK$) or leucine-lysine peptide mixture (LK) were examined for their effect on MRSA biofilm biomass degradation by crystal violet staining. Degradation was compared to the antibiotic Daptomycin.
Figure 3:
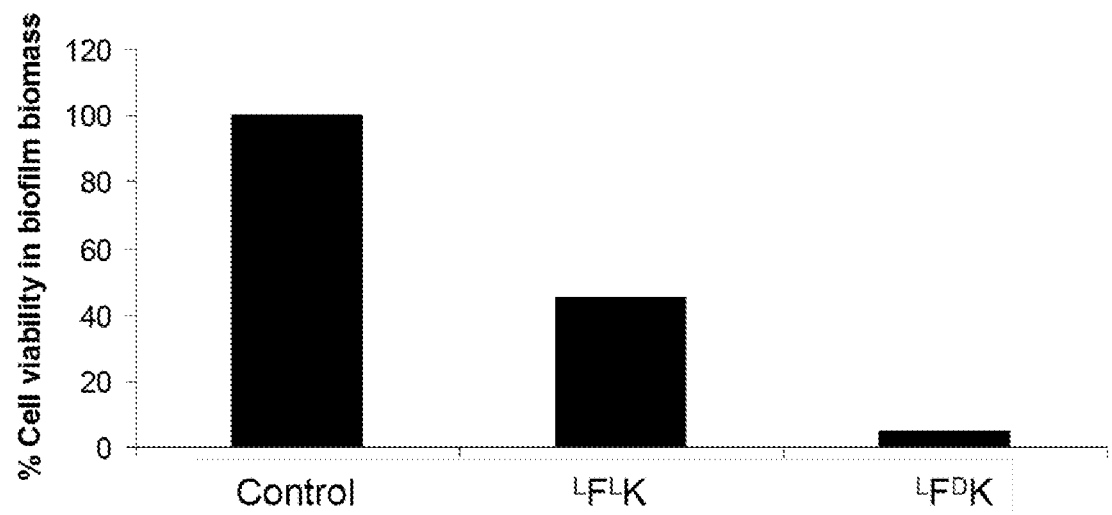
FIG. 3 shows bacterial cell viability in MRSA biofilm after treatment with phenylalanine-lysine random-sequence peptide mixture (Homochiral $^LF^LK$ or heterochiral $^LF^DK$) at a concentration of 100 μg/mL.
Figure 4:
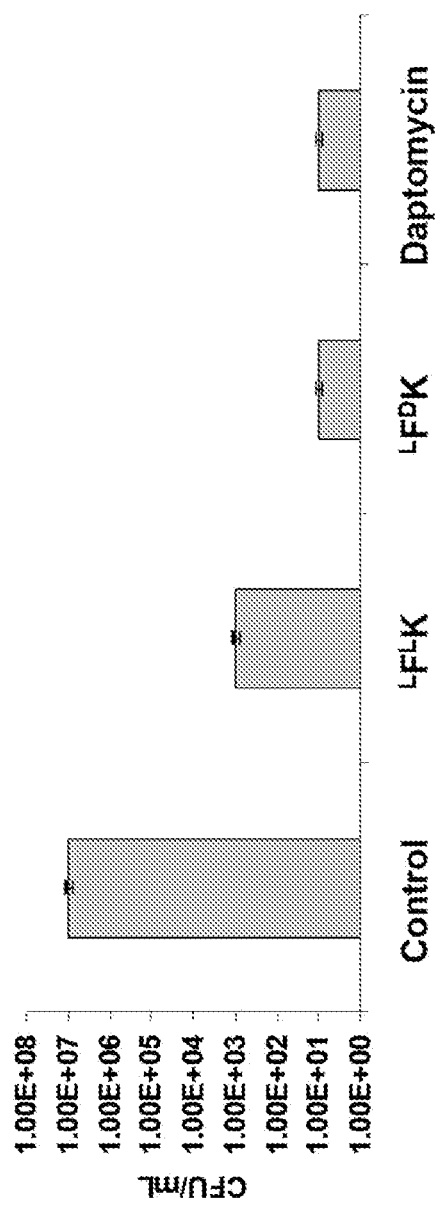
FIG. 4 shows bacterial cell counting in MRSA biofilm after treatment with the random-sequence peptide mixtures (homochiral $^LF^LK$ or heterochiral $^LF^DK$). Daptomycin was used as a positive control.

Biofilm biomass disruption was quantified using an assay that measures crystal violet absorbance at 550 nm to assess surface-attached biomass (O'Toole, G. A. et al., Mol Microbiol 1998, 30, 295-304). The results indicated that heterochiral mixture of 1:1 phenylalanine and lysine ($^LF^DK$) at 25 µg/mL showed stronger biofilm biomass disruption (22% of the biofilm biomass remained) compared to the homochiral ($^LF^LK$) mixture (55%). At a higher concentration (200 µg/mL), both random-sequence peptide mixtures (homochiral and heterochiral) were highly active (FIG. 2). The differences in the observed activity profile are probably due to the stability of the mixtures. The homochiral peptide mixture is probably more sensitive to protease activity than the heterochiral peptide mixture. Daptomycin, a lipopeptide antibiotic that is being used in the treatment of systemic and life-threatening infections caused by MRSA was used as a positive control in this study. Daptomycin was shown previously to disrupt biomass biofilm of MRSA. Biofilm biomass disruption was also evaluated for a mixture of 1:1 leucine and lysine. As shown in FIG. 2, lower activity was observed for the leucine-lysine mixture Next, XTT assay was used to quantify the cell viability of bacterial cells in the biofilm matrix after treating with the random-sequence peptides mixtures for 24 hr. The results showed that only 5% of the MRSA bacterial cells survived the treatment of the heterochiral mixture, compared to a significantly higher extent of cell survival (40%) when treated with the homochiral mixture (FIG. 3). The killing of the bacterial cell within the biofilm was further evaluated by cell counting. The biofilm biomass was sonicated and plated to measure the viability of MRSA inside the biofilm biomass after treatment. The heterochiral mixture treatment killed most of the bacterial cells within the biofilm biomass (FIG. 4).

Figures 5A, 5B, 5C:
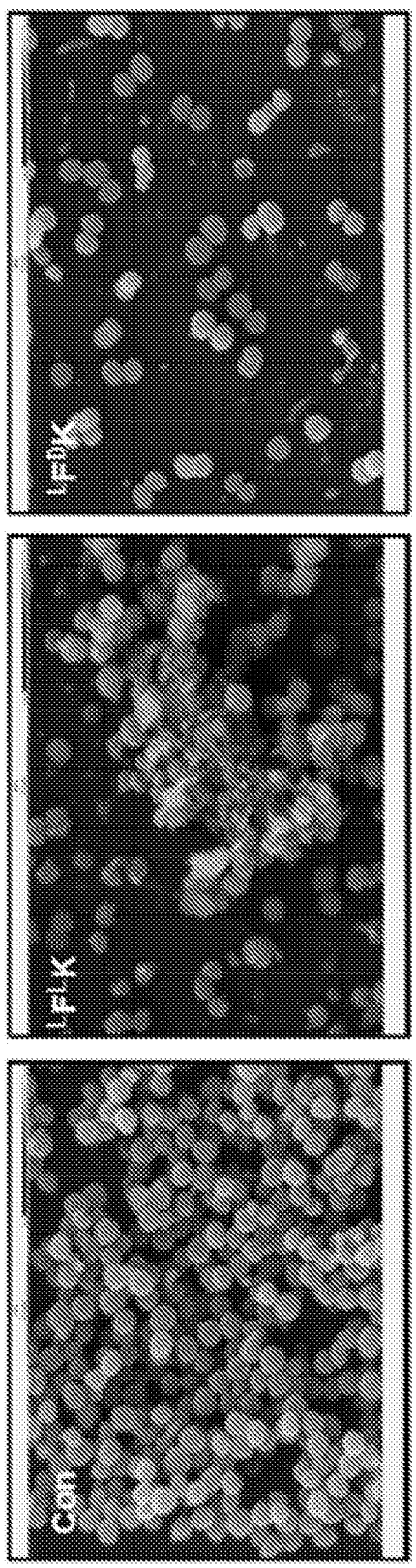
FIGS. 5A-C are scanning electron micrographs showing the effect of random-sequence peptide mixtures (homochiral $^LF^LK$ or heterochiral $^LF^DK$) on mature MRSA biofilm. A mature MRSA biofilm grown on glass disks was treated for 24 hrs with 100 μg/mL $^LF\ ^LK$ (FIG. 5B) or with $^LF^DK$ (FIG. 5C). As a control, non-treated mature MRSA biofilm is shown (FIG. 5A).

For further characterization of the ability of the mixtures to eradicate the MRSA established biofilm, a Scanning Electron Microscopy (SEM) study was performed. A mature MRSA biofilm was grown on glass disks for 48 h, then was treated with 100 µg/mL of $^LF^LK$ or $^LF^DK$ for 24 h and viewed under a scanning electron microscope (FIGS. 5A-C). As shown in the figure, $^LF^DK$ was able to remove MRSA biofilms more efficiently (FIG. 5C) compared to the homochiral mixture $^LF^LK$ (FIG. 5B).

Example 3

Effect of Random Sequence Peptide Mixtures of Tryptophan and Lysine on *B. subtilis* Forming Biofilm The effect of random sequence peptide mixture on biofilm formation was investigated using mixtures of peptides prepared with tryptophan and lysine. The anti-biofilm effect of random-sequence peptide mixtures that contain tryptophan and lysin in 4 different stereoisomeric forms ($^LW^LK$, $^LW^DK$, $^DW^LK$, $^DW^DK$) was examined on *B. subtilis* 3610.

Figures 6A, 6B:
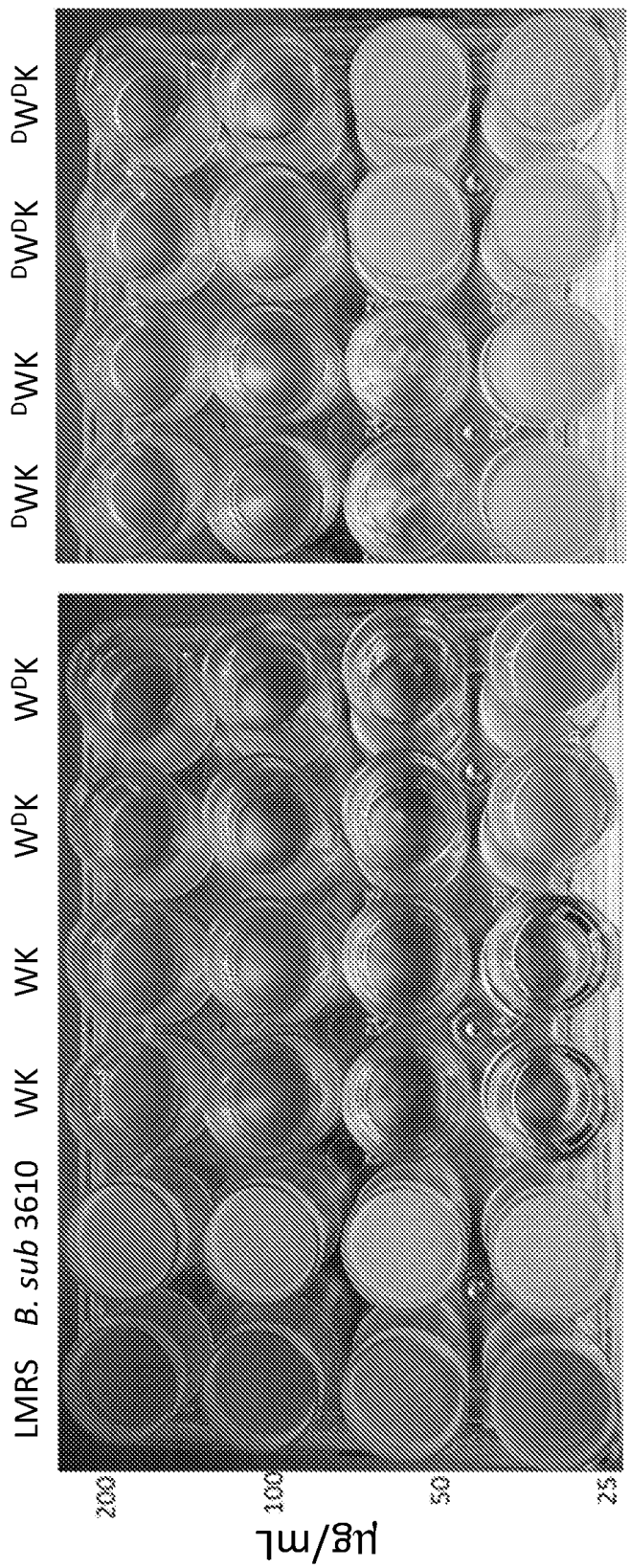
FIGS. 6A-B show the effect of homochiral or heterochiral mixtures of random-sequence peptides consisting of tryptophan and lysine (WK, $W^DK$, and $^DW^DK$) on *Bacillus subtilis* biofilm formation. Lactobacillus-MRS (LMRS) and *B. subtilis* 3610 not treated with the peptide mixtures were use as control.

The *Bacillus subtilis* wild strain NCIB3610 and *Bacillus subtilis* that was isolated from milk were used in this study. *Lactobacillus*-MRS Broth (LMRS Broth) is an enriched selective medium intended for the isolation and cultivation of *Lactobacillus* found in clinical specimens and dairy and food products. This media was found to be very effective to grow *Bacillus subtilis* pellicle, a biofilm floating at the air-liquid interface. For biofilm generation, bacteria were grown to stationary phase in LMRS at 37° C. in shaking culture to around 1×10$^8$ CFU per ml. Biofilms were generated at 30° C. in the biofilm promoting medium LMRS. As shown in FIG. 6A, a very thick biofilm was developed in the control bacteria (*B. sub* 3610 lane). In contrary, inhibition in the formation of biofilm (50 µg/mL) was observed in wells that were treated with WK, W$^D$K, or $^D$WK random peptide mixtures (FIGS. 6A-B). The $^DW^DK$ peptide mixture exhibited lower activity, wherein biofilm formation was inhibited at 100 µg/mL (FIG. 6B). These results demonstrate that the random peptide mixtures inhibit biofilm formation of *B. subtilis*.

Example 4

Random-Sequence Peptide Mixtures Penetrate MRSA Cells

Figures 7A, 7B, 7C:
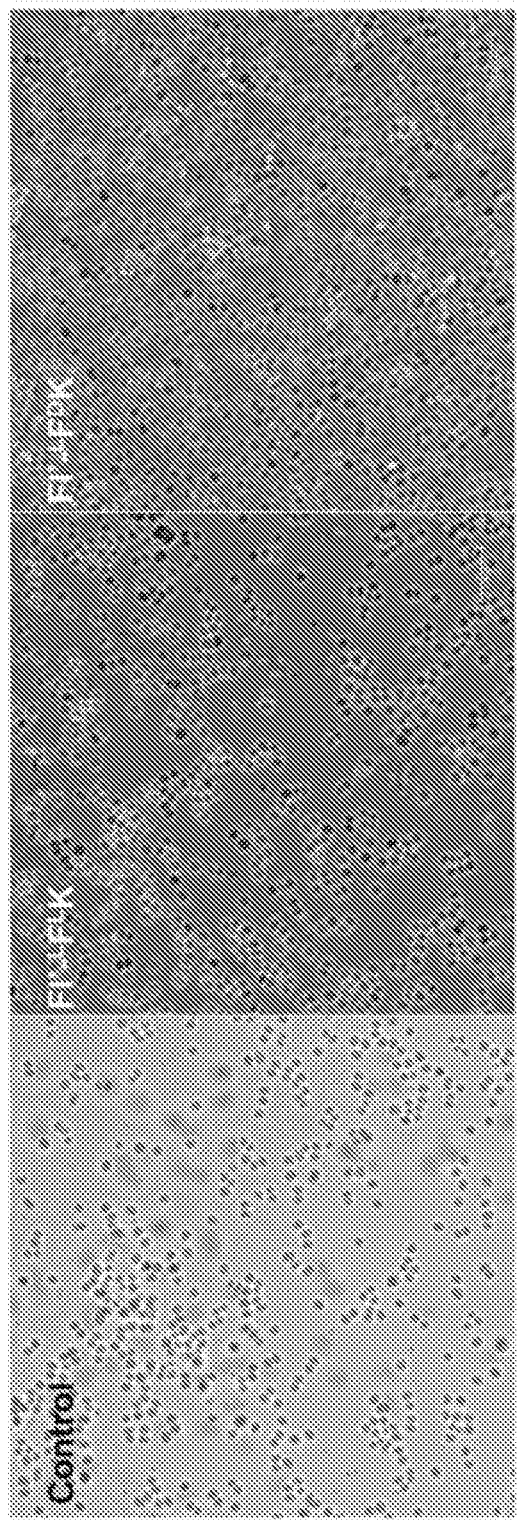
FIGS. 7A-C are representative confocal microscopy images of MRSA cells treated with labeled random-sequence peptide mixtures. Fluorescently labeled random peptide mixture (Fl'-$^L$F$^L$K or Fl'-$^L$F$^D$K) were incubated for 1 hr with MRSA cells and then photographed using confocal microscopy.

To study if the mixtures of the invention penetrate the bacterial cells, random sequence peptide mixtures ($^LF^LK$ or $^LF^DK$) were synthesized and labeled at their N' terminus free amino group with 5(6)-carboxyfluorescein. Confocal microscopy was used to determine their ability to penetrate MRSA bacterial cells (FIGS. 7A-C). After 1 h of incubation, the heterochiral and homochiral mixtures were observed in MRSA bacterial cells (FIGS. 7B and 7C, respectively). It is assumed that some of the random peptide mixtures caused damage to the bacterial membrane, and enhanced the entry of other random peptides into the bacterial cells.

Example 5

Random-Sequence Peptide Mixtures Effect on Human Cells

Figure 8:
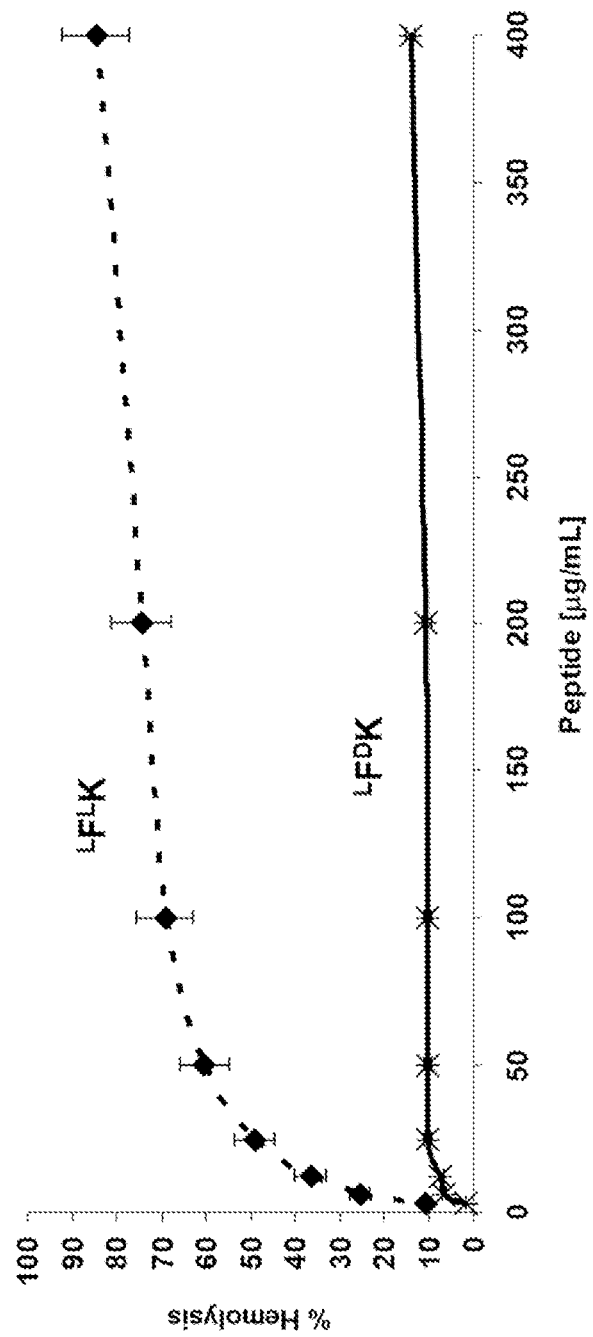
FIG. 8 shows the hemolytic activity of increasing concentrations of $^L$F$^L$K and $^L$F$^D$K towards human red blood cells.

The random peptide mixtures ($^L$F$^L$K or $^L$F$^D$K) were examined for their red blood cell hemolysis activity as described before (Hayouka et al., J. Am. Chem. Soc., 2013, 135, 11748-11751). The heterochiral peptide mixture showed lower hemolytic activity towards human red blood cells compared to the homochiral mixture (FIG. 8).

Figure 9:
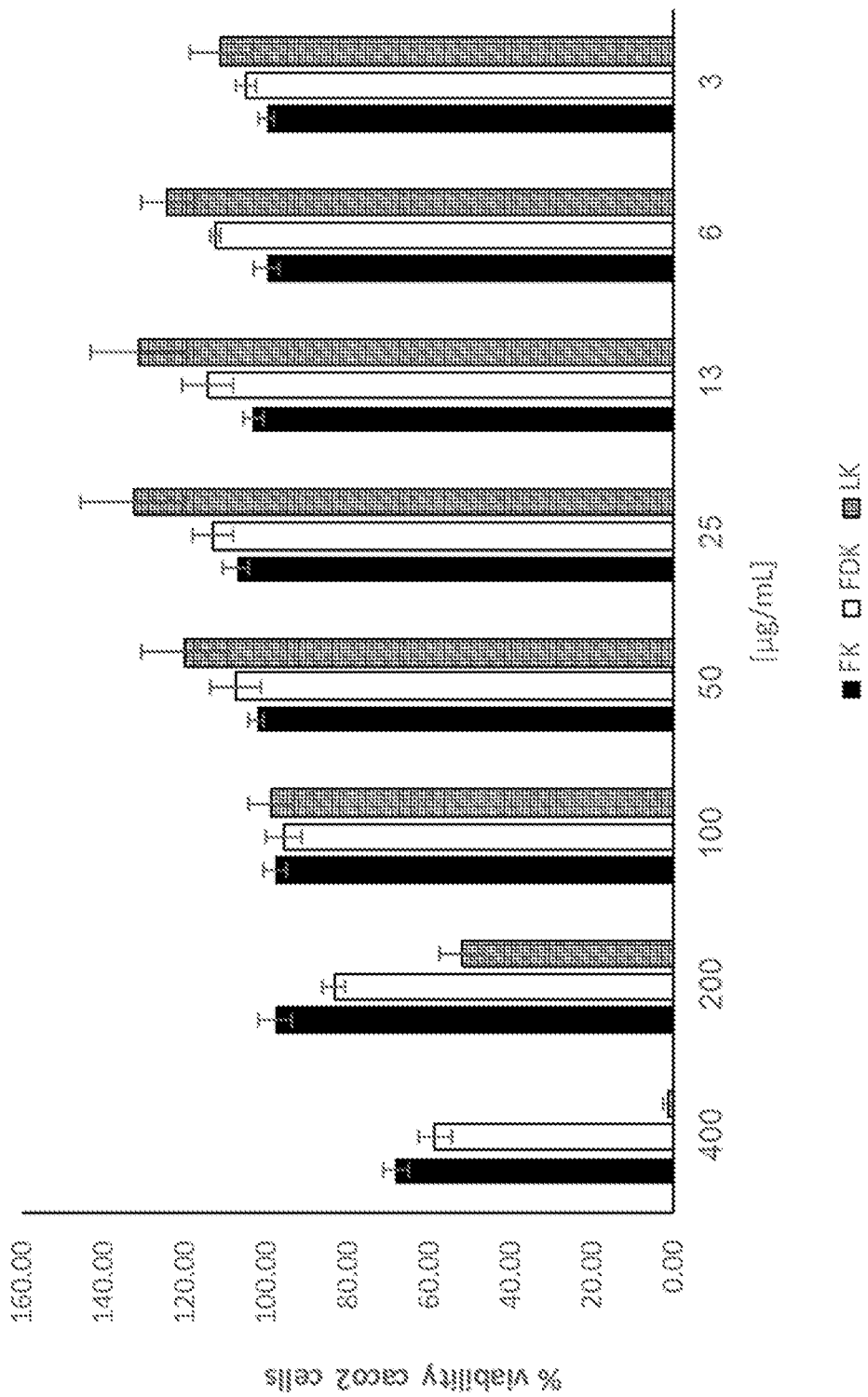
FIG. 9 shows the viability of Caco-2 cells (a human intestinal epithelial cell line) in the presence of increasing concentrations of $^L$F$^L$K, $^L$F$^D$K, and leucine lysine ($^L$L$_L$K).

The cytotoxicity of the random-sequence peptide mixtures was further tested on Caco-2 (European Collection of Animal cell Cultures, UK) cells. This human intestinal epithelial cell line was used between passages 30-50. Caco-2 cells were grown in Dulbecco's modified Eagle's medium (DMEM) with 2 mM L-glutamine, 1% (v/v) non-essential amino acids, 100 U/ml penicillin, 100 µg/ml streptomycin and 10% (v/v) fetal bovine serum (Sigma-Aldrich, Ireland). The cells were grown at 37° C. in a humidified atmosphere with 5% $CO_2$. The cytotoxic potential of the random-sequence peptide mixtures was determined following incubation of exponentially growing cells using the MTT assay. As shown in FIG. 9, random-sequence peptide mixtures ($^L$F$^L$K or $^L$F$^D$K) exhibited less cytotoxicity compared to leucine-lysine mixture at 200 and 400 µg/ml concentrations.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method of treating or preventing a biofilm-associated infection in a subject comprising administering to the subject in need of such treatment a pharmaceutical composition comprising a mixture of a plurality of random-sequence peptides and a pharmaceutically acceptable carrier, wherein the peptides have an identical number of amino acid residues and a length of 10 to 40 amino acid residues, wherein the mixture of peptides consists of one species of a hydrophobic amino acid in an L- or D-configuration and one species of a cationic amino acid in an L- or D-configuration, wherein the ratio in the mixture of the total hydrophobic and cationic amino acids is about 1:1, and wherein the mixture of the plurality of random-sequence peptides contains $2^{10}$ up to millions of sequences.

2. The method of claim 1, wherein the biofilm-associated infection is caused by unicellular organisms selected from the group consisting of bacteria, fungi, and archaea.

3. The method of claim 2, wherein the biofilm-associated infection is caused by antibiotic-resistant bacteria.

4. The method of claim 2, wherein the bacteria are selected from the group consisting of *Staphylococcus aureus, Staphylococcus epidermidis, Bacillus subtilus, Bacillus cereus, Streptococcus mutans, E. coli, Listeria, Salmonella* and *Pseudomonas aeruginosa*.

5. The method of claim 3, wherein the antibiotic-resistant bacteria are methicillin-resistant *Staphylococcus aureus* (MRSA).

6. The method of claim 1, wherein the hydrophobic amino acid is selected from the group consisting of phenylalanine and leucine.

7. The method of claim 1, wherein the cationic amino acid is lysine.

8. The method of claim 1, wherein the mixture comprises heterochiral peptides.

9. The method of claim 1, wherein the hydrophobic amino acid is phenylalanine and the cationic amino acid is lysine.

10. The method of claim 1, wherein the number of the amino acid residues ranges between 15 and 25.

11. The method of claim 1, wherein the pharmaceutical composition further comprises an antimicrobial agent.

12. The method of claim 1, wherein the biofilm-associated infection is selected from the group consisting of skin infections, stomach infections, urinary tract infections, and infections associated with indwelling devices.

13. The method of claim 1, wherein the biofilm-associated infection is selected from the group consisting of cutaneous wound infections, middle-ear infections, dental plaque infection, gingivitis, endocarditis, and pneumonia.

14. A method for preventing biofilm formation, which method comprises applying to a surface of an item a composition comprising an effective amount of a mixture of a plurality of random-sequence peptides, wherein the peptides have an identical number of amino acid residues and a length of 10 to 40 amino acid residues, wherein the mixture of peptides consists of one species of a hydrophobic amino acid in an L- or D-configuration and one species of a cationic amino acid in an L- or D-configuration, wherein the ratio in the mixture of the total hydrophobic and cationic amino acids is about 1:1, and wherein the mixture of the plurality of random-sequence peptides contains $2^{10}$ up to millions of sequences.

15. The method of claim 14, wherein the item is a medical device, catheter, or an implant.

16. The method of claim 14, wherein the surface of an item is a food processing surface.

17. The method of claim 14, wherein the item is a commercial and/or industrial water system.

* * * * *